United States Patent
Li et al.

(10) Patent No.: US 8,447,390 B2
(45) Date of Patent: May 21, 2013

(54) DETECTING HEMODYNAMIC STABILITY DURING ARRHYTHMIA USING THE CHANGES IN ATRIAL ACTIVATION

(71) Applicants: Dan Li, Shoreview, MN (US); Arjun D. Sharma, St. Paul, MN (US)

(72) Inventors: Dan Li, Shoreview, MN (US); Arjun D. Sharma, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/650,376

(22) Filed: Oct. 12, 2012

(65) Prior Publication Data
US 2013/0035605 A1 Feb. 7, 2013

Related U.S. Application Data (63) Continuation of application No. 13/021,905, filed on Feb. 7, 2011, now Pat. No. 8,346,350.

(60) Provisional application No. 61/302,730, filed on Feb. 9, 2010.

(51) Int. Cl.
*A61B 5/0464* (2006.01)

(52) U.S. Cl.
USPC ............................ 600/515; 600/518; 607/4

(58) Field of Classification Search
USPC ............................ 600/509, 515, 518; 607/4
See application file for complete search history.

(56) References Cited

U.S. PATENT DOCUMENTS

| 5,107,850 A | 4/1992 | Olive |
| 5,205,283 A | 4/1993 | Olson |
| 2009/0131996 A1 | 5/2009 | Li |
| 2011/0196439 A1 | 8/2011 | Li et al. |

FOREIGN PATENT DOCUMENTS

| WO | WO-2009064222 A1 | 5/2009 |
| WO | WO-2011100182 A1 | 8/2011 |

OTHER PUBLICATIONS

"U.S. Appl. No. 13/021,905, Notice of Allowance mailed Aug. 27, 2012", 8 pgs.
"U.S. Appl. No. 13/021,905, Preliminary Amendment filed May 11, 2012", 15 pgs.
"International Application Serial No. PCT/US2011/023864, International Preliminary Report on Patentability mailed Apr. 26, 2012", 16 pgs.
"International Application Serial No. PCT/US2011/023864, International Search Report mailed May 16, 2011", 6 pgs.
"International Application Serial No. PCT/US2011/023864, Written Opinion mailed Feb. 10, 2012", 7 pgs.
"International Application Serial No. PCT/US2011/023864, Written Opinion mailed May 16, 2011", 7 pgs.
Hegbom, F., et al., "RV Function in Stable and Unstable VT: is There a Need for Hemodynamic Monitoring in Future Defibrillators?", Pacing and Clinical Electrophysiology, 24(2), (Feb. 2001), 172-182.
Militianu, A., et al., "Ventriculoatrial conduction capability and prevalence of 1:1 retrograde conduction during inducible sustained monomorphic ventricular tachycardia in 305 implantable cardioverter defibrillator recipients.", Pacing Clin Electrophysiol., 20(10 Pt 1), (Oct. 1997), 2378-84.
Smith, M. L, et al., "Reflex control of sympathetic activity during ventricular tachycardia in dogs: primary role of arterial baroreflexes", Circulation, 93(5), (Mar. 1, 1996), 1033-42.

*Primary Examiner* — Joseph Dietrich
(74) *Attorney, Agent, or Firm* — Schwegman Lundberg & Woessner, P.A.

(57) ABSTRACT

Detected changes in atrial activation can be used to discriminate between hemodynamically stable and hemodynamically unstable tachyarrhythmias.

18 Claims, 9 Drawing Sheets

DETECTING HEMODYNAMIC STABILITY DURING ARRHYTHMIA USING THE CHANGES IN ATRIAL ACTIVATION

CLAIM OF PRIORITY

This application is a continuation of and claims the benefit of priority under 35 U.S.C. §120 to U.S. patent application Ser. No. 13/021,905, filed on Feb. 7, 2011, now issued as U.S. Pat. No. 8,346,350, which claims the benefit of priority under 35 U.S.C. §119(e) of U.S. Provisional Application No. 61/302,730, filed on Feb. 9, 2010, under 35 U.S.C. §119(e), the benefit of priority of each of which is claimed hereby, and each of which are incorporated by reference herein in its entirety.

BACKGROUND

Implantable medical devices (IMDs) are devices designed to be implanted into a patient. Some examples of these devices include cardiac rhythm management (CRM) devices. CRM devices include implantable pacemakers, implantable cardioverter defibrillators (ICDs), and devices that include a combination of pacing and defibrillation including cardiac resynchronization therapy. The devices are typically used to treat patients using electrical therapy and to aid a physician or caregiver in patient diagnosis through internal monitoring of a patient's condition. The devices can include electrical leads in communication with sense amplifiers to monitor electrical heart activity within a patient, and often include sensors to monitor other internal patient parameters. Other examples of implantable medical devices include implantable insulin pumps or devices implanted to administer drugs to a patient.

Additionally, some IMDs detect events by monitoring electrical heart activity signals. By monitoring cardiac signals, IMDs are able to detect abnormally rapid heart rate, or tachyarrhythmia. Although detecting an occurrence of tachyarrhythmia is important, it can be even more helpful if additional physiologic information is known about the tachyarrhythmia, such as if the tachyarrhythmia is hemodynamically stable or unstable. An IMD that can not only detect tachyarrhythmias, but also discriminate between hemodynamically stable and unstable tachyarrhythmias, can be used to help guide therapy decisions.

OVERVIEW

This document describes, among other things, systems and methods for discriminating between hemodynamically stable and hemodynamically unstable tachyarrhythmias using detected changes in atrial activation.

Example 1 can include subject matter that can include an apparatus comprising: a cardiac rhythm management device comprising: an atrial activation sensing circuit configured to sense an atrial activation of a subject; a tachyarrhythmia detection circuit configured to detect whether tachyarrhythmia is present in a subject; and a processor circuit, coupled to the atrial activation sensing circuit and the tachyarrhythmia detection circuit, the processor configured to: compare a characteristic of the atrial activation present just before the tachyarrhythmia was detected to a characteristic of the atrial activation during the detected tachyarrhythmia; and use the comparison to determine a hemodynamic stability characteristic of the tachyarrhythmia.

In Example 2, the subject matter of Example 1 can optionally include the characteristic of the atrial activation including at least one of: an atrial rate or interval, or an atrial or interval variability.

In Example 3, the subject matter of any one of Examples 1-2 can optionally include the characteristic of the atrial activation being determined over multiple cardiac cycles.

In Example 4, the subject matter of any one of Examples 1-3 can optionally include the processor configured to: compare an atrial rate present just before the tachyarrhythmia was detected to an atrial rate during the detected tachyarrhythmia; determine that the atrial rate during the detected tachyarrhythmia is not substantially increased from the atrial rate present just before the tachyarrhythmia was detected; and declare that the tachyarrhythmia is hemodynamically stable when it is determined that the atrial rate during the detected tachyarrhythmia is not substantially increased from the atrial rate present just before the tachyarrhythmia was detected.

In Example 5, the subject matter of any one of Examples 1-4 can optionally include the processor configured to: compare an atrial rate present just before the tachyarrhythmia was detected to an atrial rate during the detected tachyarrhythmia; determine that the atrial rate during the detected tachyarrhythmia is substantially increased from the atrial rate present just before the tachyarrhythmia was detected; and declare that the tachyarrhythmia is hemodynamically unstable when it is determined that the atrial rate during the detected tachyarrhythmia is substantially increased from the atrial rate present just before the tachyarrhythmia was detected.

In Example 6, the subject matter of any one of Examples 1-5 can optionally include the processor configured to: determine a difference between an atrial rate variability present just before the tachyarrhythmia was detected to an atrial rate variability during the detected tachyarrhythmia; compare the difference to a threshold value; when the difference is above the threshold value, declare that the tachyarrhythmia is hemodynamically stable; and when the difference is below the threshold value, declare that the tachyarrhythmia is hemodynamically unstable.

In Example 7, the subject matter of any one of Examples 1-6 can optionally include the processor configured to, in response to a detected tachyarrhythmia, determine whether the sensed atrial rate exceeds a threshold value; and when the sensed atrial rate exceeds the threshold value, declare the tachyarrhythmia to be hemodynamically unstable; and when the sensed atrial rate is less than the threshold value, declare the tachyarrhythmia to be hemodynamically stable.

In Example 8, the subject matter of any one of Examples 1-7 can optionally include the processor configured to trigger communication an indication of the hemodynamic stability characteristic of the tachyarrhythmia to a user interface or process.

In Example 9, the subject matter of any one of Examples 1-8 can optionally include a therapy circuit, coupled to the processor, the therapy circuit configured to provide therapy to the subject; wherein the processor is configured to use the hemodynamic stability characteristic of the tachyarrhythmia to control therapy provided to the subject.

In Example 10, the subject matter of any one of Examples 1-9 can optionally include the therapy circuit configured to provide anti-tachyarrhythmia pacing to the subject when the tachyarrhythmia is hemodynamically stable.

In Example 11, the subject matter of any one of Examples 1-10 can optionally include the therapy circuit configured to provide shock therapy to the subject when the tachyarrhythmia is hemodynamically unstable.

In Example 12, the subject matter of any one of Examples 1-11 can optionally include the therapy circuit configured to withhold shock therapy when the tachyarrhythmia is hemodynamically stable.

In Example 13, the subject matter of any one of Examples 1-12 can optionally include a therapy circuit, coupled to the processor, the therapy circuit configured to deliver therapy to the subject in response to a detected tachyarrhythmia; wherein the processor is configured to: compare an atrial characteristic present during the tachyarrhythmia and just before delivery of therapy to an atrial characteristic present during or after delivery of therapy; and use the comparison to do at least one of: 1) confirm or detect a change in the hemodynamic stability characteristic of the tachyarrhythmia, or 2) adjust the therapy.

Example 14 can include, or can optionally be combined with any one of Examples 1-13 to include subject matter that can include an apparatus comprising: a cardiac rhythm management device comprising: an atrial rate sensing circuit configured to sense an atrial rate of a subject; a tachyarrhythmia detection circuit configured to detect whether tachyarrhythmia is present in a subject; and a processor circuit, coupled to the atrial rate sensing circuit and the tachyarrhythmia detection circuit, the processor configured to: detect an atrial rate trend present at least 5 seconds after the start of the detected tachyarrhythmia; determine whether the atrial rate trend present at least 5 seconds after the start of the detected tachyarrhythmia is increasing or decreasing; and use the determination to declare a hemodynamic stability characteristic of the tachyarrhythmia.

In Example 15, the subject matter of any one of Examples 1-14 can optionally include the processor circuit configured to declare that the tachyarrhythmia is hemodynamically unstable when it is determined that the atrial rate trend present at least 5 seconds after the start of the detected tachyarrhythmia is increasing.

In Example 16, the subject matter of any one of Examples 1-15 can optionally include the processor circuit configured to declare that the tachyarrhythmia is hemodynamically stable when it is determined that the atrial rate trend present at least 5 seconds after the start of the detected tachyarrhythmia is decreasing.

In Example 17, the subject matter of any one of Examples 1-16 can optionally include the atrial rate trend being determined over multiple cardiac cycles.

In Example 18, the subject matter of any one of Examples 1-17 can optionally include the processor configured to trigger communication an indication of the hemodynamic stability characteristic of the tachyarrhythmia to a user interface or process.

In Example 19, the subject matter of any one of Examples 1-18 can optionally include a therapy circuit, coupled to the processor, the therapy circuit configured to provide therapy to the subject; wherein the processor is configured to use the hemodynamic stability characteristic of the tachyarrhythmia to control therapy provided to the subject.

In Example 20, the subject matter of any one of Examples 1-19 can optionally include the therapy circuit configured to provide anti-tachyarrhythmia pacing to the subject when the tachyarrhythmia is hemodynamically stable.

In Example 21, the subject matter of any one of Examples 1-20 can optionally include the therapy circuit configured to provide shock therapy to the subject when the tachyarrhythmia is hemodynamically unstable.

In Example 22, the subject matter of any one of Examples 1-21 can optionally include the therapy circuit configured to withhold shock therapy when the tachyarrhythmia is hemodynamically stable.

In Example 23, the subject matter of any one of Examples 1-22 can optionally include a therapy circuit, coupled to the processor, the therapy circuit configured to deliver therapy to the subject in response to a detected tachyarrhythmia; wherein the processor is configured to: compare an atrial rate trend present during the tachyarrhythmia and just before delivery of therapy to an atrial rate trend present during or after delivery of therapy; and use the comparison to do at least one of: 1) confirm or detect a change in the hemodynamic stability characteristic of the tachyarrhythmia, or 2) adjust the therapy.

Example 24 can include, or can optionally be combined with any one of Examples 1-23 to include subject matter that can include sensing an atrial activation of a subject; detecting that a tachyarrhythmia is present in the subject; comparing a characteristic of the atrial activation present just before the tachyarrhythmia was detected to a characteristic of the atrial activation during the detected tachyarrhythmia; and using the comparison to determine a hemodynamic stability characteristic of the tachyarrhythmia.

In Example 25, the subject matter of any one of Examples 1-24 can optionally include the characteristic of the atrial activation including at least one of: an atrial rate or interval, or an atrial rate or interval variability.

In Example 26, the subject matter of any one of Examples 1-25 can optionally include the characteristic of the atrial activation being determined over multiple cardiac cycles.

In Example 27, the subject matter of any one of Examples 1-26 can optionally include comparing an atrial rate present just before the tachyarrhythmia was detected to an atrial rate during the detected tachyarrhythmia; determining that the atrial rate during the detected tachyarrhythmia is not substantially increased from the atrial rate present just before the tachyarrhythmia was detected; and declaring that the tachyarrhythmia is hemodynamically stable upon determining that the atrial rate during the detected tachyarrhythmia is not substantially increased from the atrial rate present just before the tachyarrhythmia was detected.

In Example 28, the subject matter of any one of Examples 1-27 can optionally include comparing an atrial rate present just before the tachyarrhythmia was detected to an atrial rate during the detected tachyarrhythmia; determining that the atrial rate during the detected tachyarrhythmia is substantially increased from the atrial rate present just before the tachyarrhythmia was detected; and declaring that the tachyarrhythmia is hemodynamically unstable upon determining that the atrial rate during the detected tachyarrhythmia is substantially increased from the atrial rate present just before the tachyarrhythmia was detected.

In Example 29, the subject matter of any one of Examples 1-28 can optionally include determining a difference between an atrial rate variability present just before the tachyarrhythmia was detected to an atrial rate variability during the detected tachyarrhythmia; comparing the difference to a threshold value; when the difference is above the threshold value, declaring that the tachyarrhythmia is hemodynamically stable; and when the difference is below the threshold value, declaring that the tachyarrhythmia is hemodynamically unstable.

In Example 30, the subject matter of any one of Examples 1-29 can optionally include: in response to detecting that the tachyarrhythmia is present, determining whether the sensed atrial rate exceeds a threshold value; and when the sensed atrial rate exceeds the threshold value, declaring the tachyarrhythmia to be hemodynamically unstable; and when the sensed atrial rate is less than the threshold value, declaring the tachyarrhythmia to be hemodynamically stable.

In Example 31, the subject matter of any one of Examples 1-30 can optionally include communicating an indication of the hemodynamic stability characteristic of the tachyarrhythmia to a user interface or process.

In Example 32, the subject matter of any one of Examples 1-31 can optionally include using the hemodynamic stability characteristic of the tachyarrhythmia to control therapy provided to the subject.

In Example 33, the subject matter of any one of Examples 1-32 can optionally include providing anti-tachyarrhythmia pacing to the subject when the tachyarrhythmia is hemodynamically stable.

In Example 34, the subject matter of any one of Examples 1-33 can optionally include providing shock therapy to the subject when the tachyarrhythmia is hemodynamically unstable.

In Example 35, the subject matter of any one of Examples 1-34 can optionally include withholding shock therapy when the tachyarrhythmia is hemodynamically stable.

In Example 36, the subject matter of any one of Examples 1-35 can optionally include delivering therapy to the subject in response to a detected tachyarrhythmia; comparing an atrial characteristic present during the tachyarrhythmia and just before delivery of therapy to an atrial characteristic present during or after delivery of therapy; and using the comparison to do at least one of: 1) confirm or detect a change in the hemodynamic stability characteristic of the tachyarrhythmia, or 2) adjust the therapy.

Example 37 can include, or can optionally be combined with any one of Examples 1-36 to include subject matter that can include sensing an atrial rate of a subject; detecting that a tachyarrhythmia is present in the subject; detecting an atrial rate trend present at least 5 seconds after the start of the detected tachyarrhythmia; determining whether the atrial rate trend present at least 5 seconds after the start of the detected tachyarrhythmia is increasing or decreasing; and using the determination to declare a hemodynamic stability characteristic of the tachyarrhythmia.

In Example 38, the subject matter of any one of Examples 1-37 can optionally include declaring that the tachyarrhythmia is hemodynamically unstable upon determining that the atrial rate trend present at least 5 seconds after the start of the detected tachyarrhythmia is increasing.

In Example 39, the subject matter of any one of Examples 1-38 can optionally include declaring that the tachyarrhythmia is hemodynamically stable upon determining that the atrial rate trend present at least 5 seconds after the start of the detected tachyarrhythmia is decreasing.

In Example 40, the subject matter of any one of Examples 1-39 can optionally include the atrial rate trend being determined over multiple cardiac cycles.

In Example 41, the subject matter of any one of Examples 1-40 can optionally include communicating an indication of the hemodynamic stability characteristic of the tachyarrhythmia to a user interface or process.

In Example 42, the subject matter of any one of Examples 1-41 can optionally include using the hemodynamic stability characteristic of the tachyarrhythmia to control therapy provided to the subject.

In Example 43, the subject matter of any one of Examples 1-42 can optionally include providing anti-tachyarrhythmia pacing to the subject when the tachyarrhythmia is hemodynamically stable.

In Example 44, the subject matter of any one of Examples 1-43 can optionally include providing shock therapy to the subject when the tachyarrhythmia is hemodynamically unstable.

In Example 45, the subject matter of any one of Examples 1-44 can optionally include withholding shock therapy when the tachyarrhythmia is hemodynamically stable.

In Example 46, the subject matter of any one of Examples 1-45 can optionally include delivering therapy to the subject in response to a detected tachyarrhythmia; comparing an atrial rate trend present during the tachyarrhythmia and just before delivery of therapy to an atrial rate trend present during or after delivery of therapy; and using the comparison to do at least one of: 1) confirm or detect a change in the hemodynamic stability characteristic of the tachyarrhythmia, or 2) adjust the therapy.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The baroreflex, or baroreceptor reflex, is one of the body's homeostatic mechanisms for maintaining blood pressure. It provides a negative feedback loop in which an elevated blood pressure can reflexively cause blood pressure to decrease. More specifically, elevated blood pressure can cause an increase in baroreceptor firing rate, which can lead to increased parasympathetic activity and decreased sympathetic activity. This, in turn, can lead to a decreased firing rate of the sinoatrial (SA) node, decreased cardiac contractility, and increased vasodilation—all of which can ultimately result in decreased cardiac output and decreased blood pressure. Similarly, a decreased blood pressure can depress the baroreflex, providing a negative feedback loop that results in increased blood pressure.

The baroreflex can contribute to the recovery of arterial pressure during hemodynamically stable tachyarrhythmia, which is tachyarrhythmia that does not cause a significant drop in the patient's blood pressure or cardiac output. Within the first five seconds of onset of hemodynamically stable tachyarrhythmia, blood pressure can drop 20-30% from baseline due to less efficient pumping of the heart. The lowest blood pressure can occur about 5 to 10 seconds after onset, and then the blood pressure can start to recover, or increase back up toward pre-tachyarrhythmia baseline levels. It is believed that blood pressure recovery during hemodynamically stable tachyarrhythmia is a result of increased sympathetic activity due to decreased firing of the baroreceptor, which leads to vasoconstriction, increased contractility, and increased firing of the SA node, all of which cause a rise in blood pressure.

On the other hand, during hemodynamically unstable tachyarrhythmia, sensitivity of the baroreflex can be reduced and the baroreflex mechanism can fail to produce blood pressure recovery. Hemodynamically unstable tachyarrhythmia results in a significant drop in a patient's blood pressure or cardiac output, such that the global or regional perfusion is not adequate to support normal organ function. Within the first five seconds of onset of hemodynamically stable tachyarrhythmia, blood pressure can drop 50-60% from baseline due to ineffective pumping of the heart. The blood pressure can then remain low and fail to recover, despite an increased baroreceptor firing rate and increased sympathetic activity (see, e.g., Hegbom et al.). Therefore, the treatment of hemodynamically unstable tachyarrhythmia generally requires shock therapy or cardioversion, whereas hemodynamically stable tachyarrhythmia can generally be managed with anti-tachyarrhythmia pacing (ATP).

The present inventors have recognized, among other things, that hemodynamic stability or instability can be detected during tachyarrhythmia using changes in atrial activation. Changes in atrial activation, including changes in atrial rate, interval, or rate/interval variability, for example, can be reflective of the hemodynamic stability of the tachyarrhythmia via the baroreflex mechanism described above. Thus, during hemodynamically stable tachyarrhythmia, an atrial rate that is not significantly increased from baseline can reflect recovery of arterial blood pressure. However, during hemodynamically unstable tachyarrhythmia, a significantly increased atrial rate can reflect a significant decrease in blood pressure due to decreased baroreflex sensitivity or failure of the baroreflex mechanism. Discrimination between hemodynamically stable and unstable tachyarrhythmia based on changes in atrial activation can be useful in guiding treatment of the tachyarrhythmia.

As used throughout this application, and as understood by one of ordinary skill in the art, the terms "atrial rate" and "atrial interval" have an inverse relationship. Thus, a faster atrial rate corresponds to a shorter atrial interval, and a slower atrial rate corresponds to a longer atrial interval.

Figure 1:
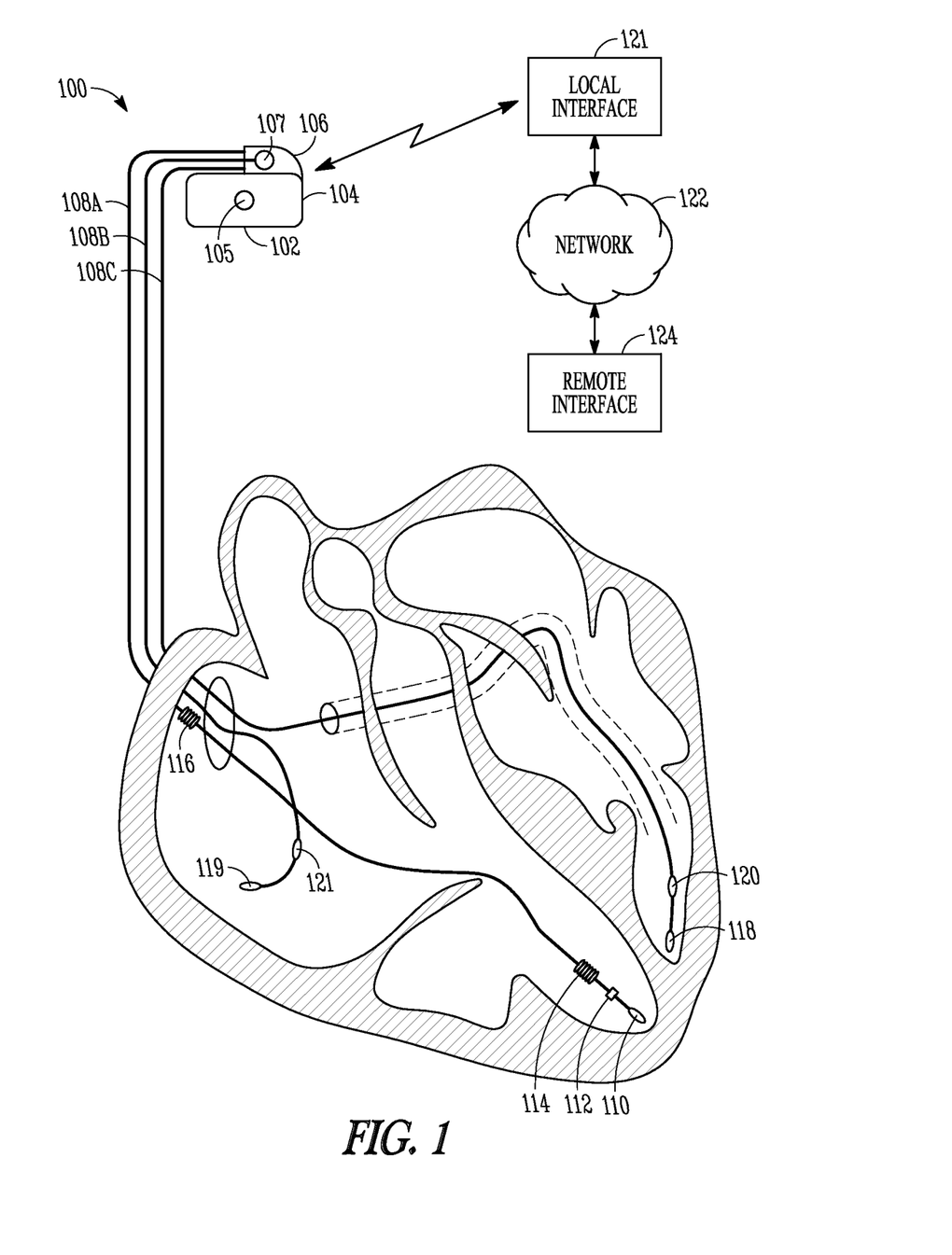
FIG. 1 shows an example of an implantable or other ambulatory cardiac rhythm management (CRM) device.

FIG. 1 shows an example of an implantable or other ambulatory cardiac rhythm management (CRM) device 100. In an example, the CRM device 100 can include an electronics unit 102 that can include a hermetically-sealed biocompatible housing 104 and a header 106 extending therefrom. The housing 104 can carry a power source and electronics. The header 106 can include one or more receptacles, such as for receiving the proximal ends of intravascular leads 108A-C. In an example, the lead 108A can be an intravascular RV lead that can extend from the superior vena cava (SVC) into the right atrium (RA), and then into the right ventricle (RV). The lead 108A can include an RV apical tip electrode 110, a slightly more proximal RV ring electrode 112, a still slightly more proximal RV shock coil electrode 114, and an even more proximal RA or SVC shock coil electrode 116. The various electrodes can be used for delivering electrical energy or sensing intrinsic electrical heart signals. An intravascular CS/LV lead 108C can extend from the SVC into the RA, through a coronary sinus (CS) into the coronary vasculature, such as near a portion of a left ventricle (LV). In an example, this second CS/LV lead 108C can include at least a distal electrode 118 and a proximal electrode 120, from which electrostimulation energies can be delivered or intrinsic electrical heart signals can be sensed. An intravascular right atrial (RA) lead 108B can extend from the SVC into the RA, and can include a distal electrode 119 and a proximal electrode 121. Other electrodes (e.g., a housing electrode 105 on the housing 104, a header electrode 107 on the header 106, an epicardial electrode, a subcutaneous electrode located away from the heart, or an electrode located elsewhere) or leads can be used.

In an example, an implantable CRM device 100 can include a communication circuit, such as to wireless communicate unidirectionally or bidirectionally with an external local interface 121, such as a CRM device programmer, repeater, handheld device, or the like. The local interface 121 can be configured to communicate via a wired or wireless computer or communication network 122 to a remote interface 124, such as a remote computer or server or the like.

Figure 2:
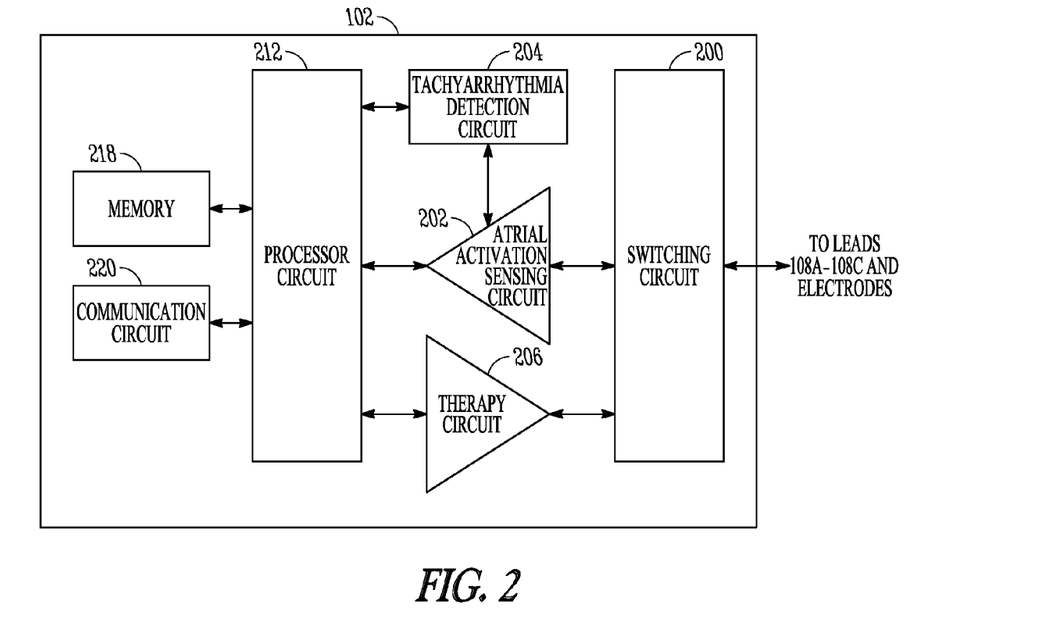
FIG. 2 shows an example of portions of the CRM device electronics unit.

FIG. 2 shows an example of portions of the CRM device electronics unit 102. In an example, this can include a switching circuit 200, such as for selectively connecting to the various electrodes such as on the leads 108A-C or elsewhere. An atrial activation sensing circuit 202 can be selectively coupled to various electrodes by the switching circuit 200, and can include sense amplifiers, filter circuits, other circuits such as for sensing intrinsic electrical signals, such as intrinsic atrial heart signals. The atrial activation sensing circuit 202 can be coupled to a tachyarrhythmia detection circuit 204. The tachyarrhythmia detection circuit 204 can be configured to detect tachyarrhythmia in a patient, such as by using heart rate or morphology information from the depolarizations sensed by the atrial activation sensing circuit 202. A therapy circuit 206 can be selectively coupled to various electrodes by the switching circuit 200, and can include pacing energy generation circuitry (e.g., capacitive, inductive, or other) such as for generating, storing, or delivering an electrostimulation, cardioversion, defibrillation, or other energy. In an example, the atrial activation sensing circuit 202, the tachyarrhythmia detection circuit 204, or the therapy circuit 206 can be coupled to a processor circuit 212. In an example, the processor 212 can perform instructions, such as for signal processing of signals derived by the atrial activation sensing circuit 202 or the tachyarrhythmia detection circuit 204, or for controlling operation of the therapy circuit 206 or other operations of the CRM device 100. The processor 212 can also be coupled to or include a memory circuit 218, such as for storing or retrieving instructions or data, or a communication circuit 220, such as for communicating with the local interface 121.

Figure 3A:
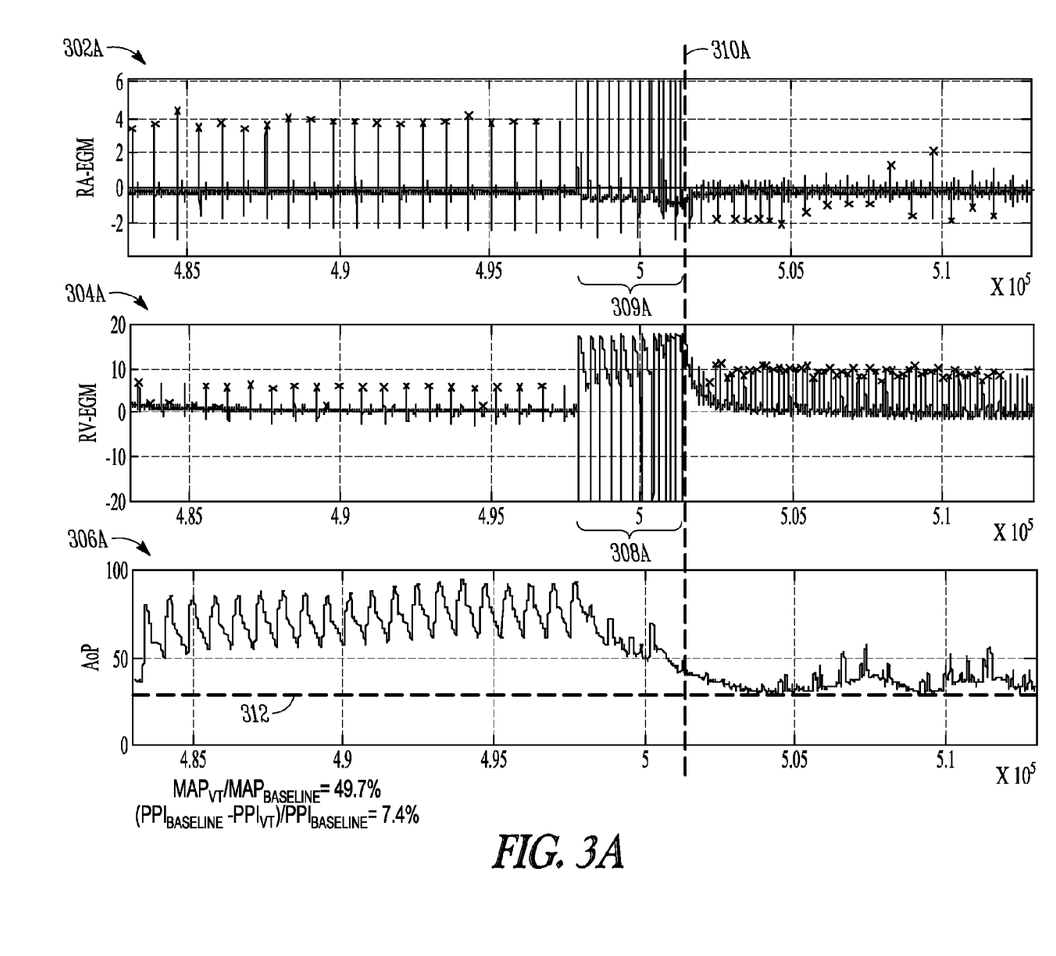
FIGS. 3A and 3B show examples of experimental animal data demonstrating the effects of induced tachyarrhythmia on atrial activation and blood pressure.
Figure 3B:
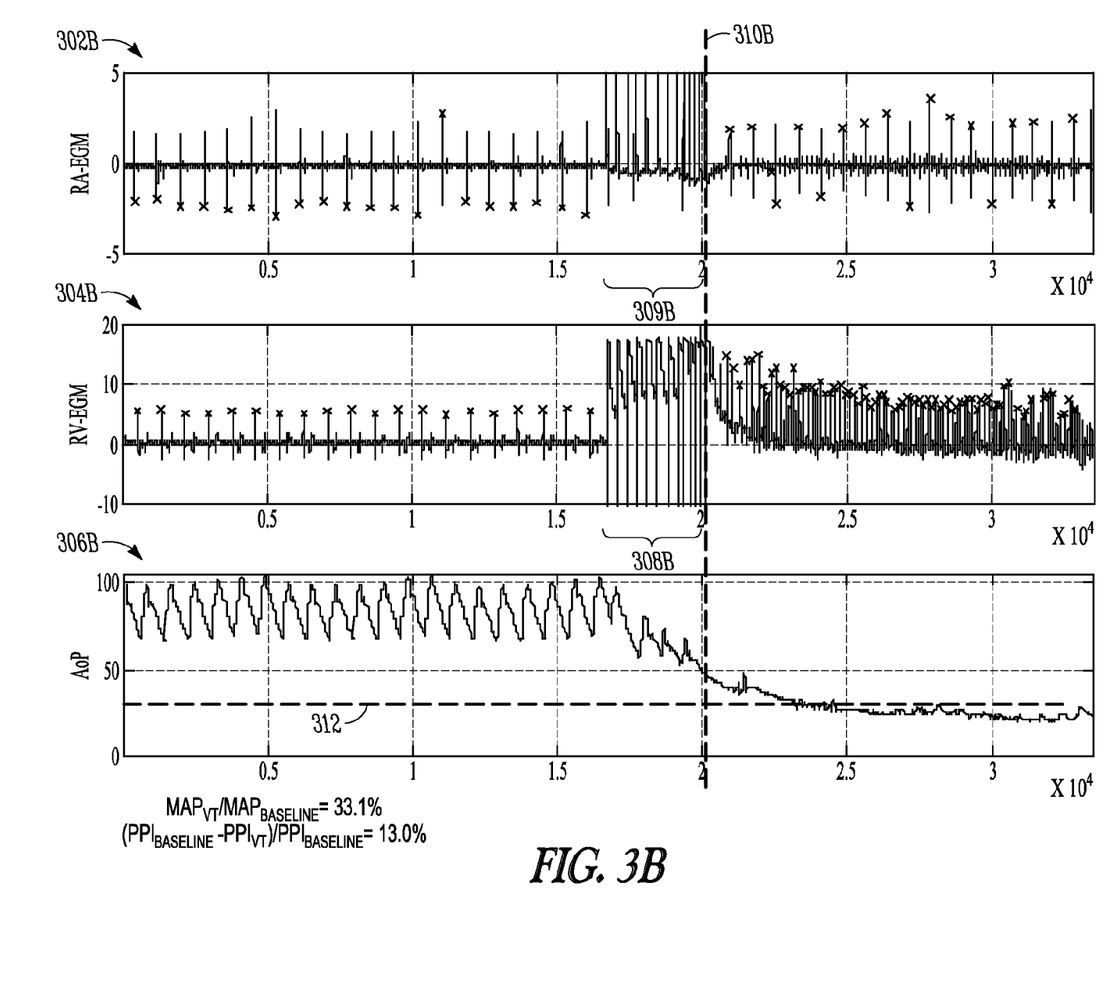

FIGS. 3A and 3B show examples of experimental animal data demonstrating the effects of induced tachyarrhythmia on atrial activation and blood pressure. FIGS. 3A and 3B contain data from one animal during two separately induced tachyarrhythmia episodes. Panels 302A and 302B illustrate right atrial activity in the animal as detected by an electrogram. Panels 304A and 304B illustrate right ventricular activity as detected by an electrogram. Panels 306A and 306B illustrate aortic pressure. At time intervals 308A and 308B, in panels 304A and 304B, respectively, ventricular pacing spikes represent the induction of ventricular tachyarrhythmia. Corresponding time intervals 309A and 309B, in panels 302A and 304B, respectively, illustrate atrial spikes that are likely due to artifacts of the ventricular pacing picked up by the atrial sensing electrodes. Vertical lines 310A and 310B represent the times at which pacing was terminated and intrinsic tachyarrhythmia began. Horizontal line 312 in panels 306A and 306B shows that the drop in aortic pressure is greater in FIG. 3B than in FIG. 3A. In FIG. 3A, mean arterial pressure (MAP) calculated from the aortic pressure signal during the tachyarrhythmia is 49.7% of the MAP at baseline (e.g., just prior to induction of tachyarrhythmia). In FIG. 3B, however, MAP during the tachyarrhythmia is only 33.1% of the MAP at baseline.

The data in FIGS. 3A and 3B illustrate that the amount by which MAP decreases during tachyarrhythmia (compared to MAP at baseline) corresponds to the amount of change in atrial activation. In FIG. 3A, the atrial P-to-P interval (PPI) is reduced by 7.4% compared to baseline, whereas in FIG. 3B the atrial PPI is reduce by 13.0% compared to baseline. Consequently, atrial rate increases more in FIG. 3B, where the drop in MAP was larger, as compared to FIG. 3A, where the drop in MAP was smaller. The greater the drop in MAP, the greater the increase in atrial rate (or decrease in atrial PPI). Thus, changes in atrial response during tachyarrhythmia can be used instead of, or in addition to, changes in MAP to detect hemodynamic stability or instability. It is believed that such a correlation is due to the baroreflex mechanism described above. Accordingly, FIG. 3A represents hemodynamically stable tachyarrhythmia, whereas FIG. 3B represents hemodynamically unstable tachyarrhythmia. In fact, an ATP burst successfully terminated the episode in FIG. 3A, and the episode in FIG. 3B required a defibrillation shock for termination.

Figure 4:
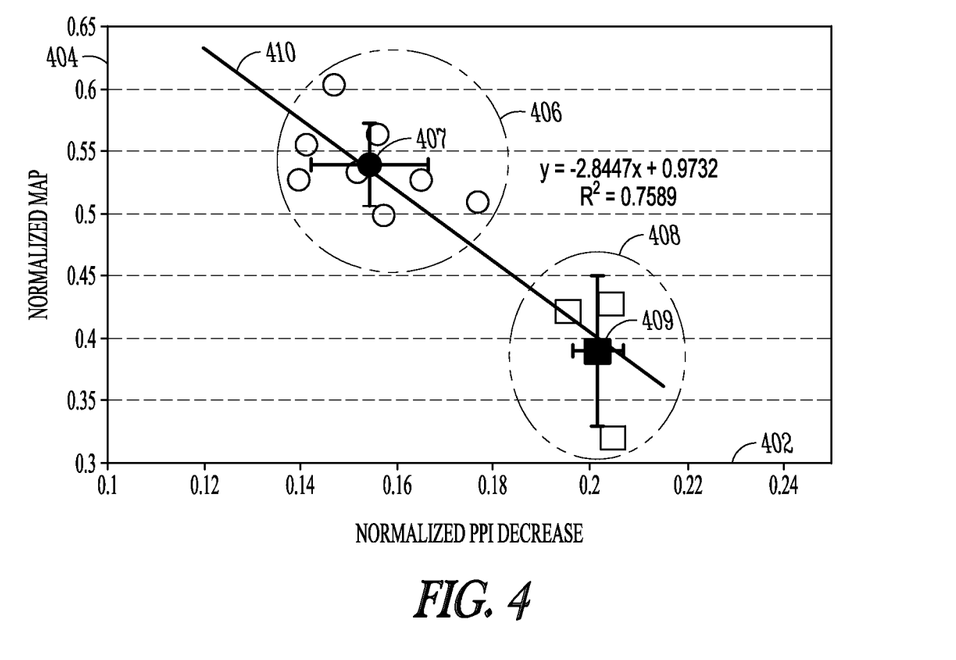
FIG. 4 shows an example of experimental animal data demonstrating a linear relationship between blood pressure and atrial interval during tachyarrhythmia.

FIG. 4 shows an example of experimental animal data demonstrating a linear relationship between blood pressure and atrial interval during tachyarrhythmia. This data was obtained from a single animal 14 days after an induced myocardial infarction via occlusion of the left anterior descending coronary artery. Eleven separately induced ventricular tachyarrhythmia episodes are plotted. Normalized atrial PPI decrease is represented along the x-axis 402. Normalized atrial PPI decrease was calculated by dividing the difference between the PPI at baseline (e.g., just prior to tachyarrhythmia induction) and the PPI during tachyarrhythmia by the PPI at baseline. Normalized MAP is represented along the y-axis 404. Normalized MAP was calculated by dividing the MAP during tachyarrhythmia by the MAP at baseline.

The group of induced tachyarrhythmia episodes plotted at 406 can be represented by averaged data point 407. Likewise, the group of induced tachyarrhythmia episodes plotted at 408 can be represented by averaged data point 409. The tachyarrhythmia episodes plotted at 406 show a moderate decrease in normalized MAP and a moderate decrease in normalized atrial PPI, which corresponds to a moderate increase in atrial rate. The tachyarrhythmia episodes plotted at 408 show a significant decrease in normalized MAP and a significant decrease in normalized atrial PPI, which corresponds to a significant increase in atrial rate. This data suggests that the tachyarrhythmia episodes plotted at 406 are likely to be hemodynamically stable and the tachyarrhythmia episodes plotted at 408 are likely to be hemodynamically unstable. In fact, the episodes plotted at 406 were terminated by ATP and the episodes plotted at 408 required shock therapy, which tends to confirm the suggested hemodynamic characterizations. The linear regression line 410 fitted to the plotted tachyarrhythmia episodes has an $R^2$ value of 0.7589, suggesting a relatively strong correlation between atrial activation and the decrease in MAP during tachyarrhythmia. Moreover, the fact that the tachyarrhythmia episodes plotted at 406 (e.g., hemodynamically stable) are well separated from the tachyarrhythmia episodes plotted at 408 (e.g., hemodynamically unstable) demonstrates that changes in atrial activation—either alone or in conjunction with changes in blood pressure—can be used to differentiate hemodynamically stable tachyarrhythmias from hemodynamically unstable tachyarrhythmias.

Figure 5:
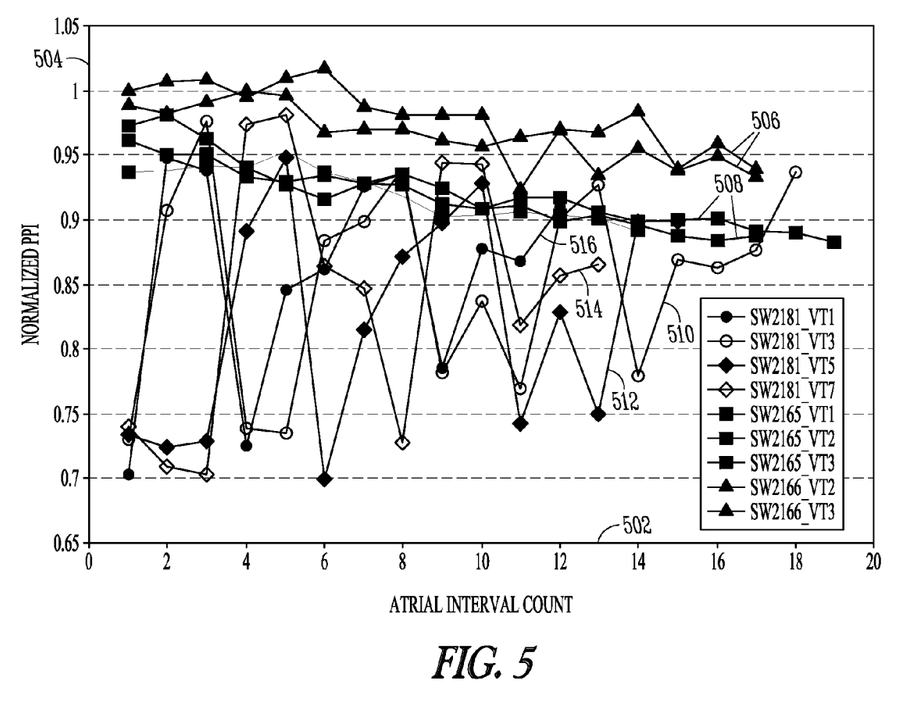
FIG. 5 shows examples of experimental animal data demonstrating differences in the variability of atrial activation during hemodynamically stable and unstable tachyarrhythmias.

FIG. 5 shows examples of experimental animal data demonstrating differences in the variability of atrial activation during hemodynamically stable and unstable tachyarrhythmias. The x-axis 502 represents atrial interval count, and the y-axis 504 represents normalized atrial PPI. The lines labeled 506 contain data points illustrated as filled triangles. The lines labeled 508 contain data points illustrated as filled squares. Lines 506 and 508 show low variability of the normalized PPI (or atrial rate) over time. In addition, lines 506 and 508 show a relatively constant normalized PPI (or atrial rate) with no recovery over time. The low variability and absence of recovery suggests that the data used to produce lines 506 and 508 came from animals with hemodynamically unstable tachyarrhythmia. In these animals, the baroreflex can be less sensitive and unable to appropriately control atrial activation in response to ventricular tachyarrhythmia. However, lines 510, 512, 514, and 516 (illustrated by open circles, filled diamonds, open diamonds, and filled circles, respectively), demonstrate high variability, as well as gradual recovery of normalized atrial PPI (or atrial rate). Thus, the data used to form lines 510, 512, 514, and 516 suggests hemodynamically stable tachyarrhythmia. The animals from which this data was obtained can have preserved baroreflex-mediated control of atrial activation in response to ventricular tachyarrhythmia.

Figure 6A:
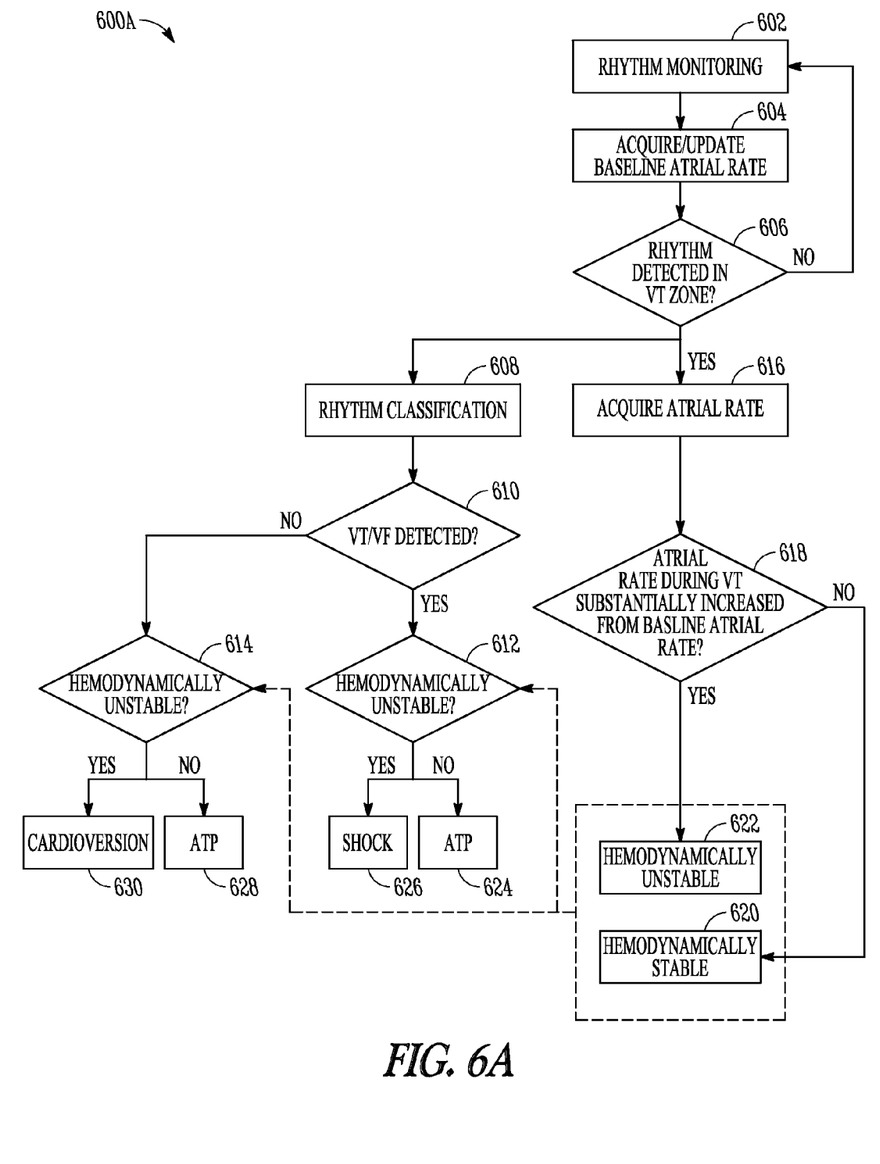
FIGS. 6A-6C show examples of methods for detecting hemodynamic stability during tachyarrhythmia using changes in atrial activation.
Figure 6B:
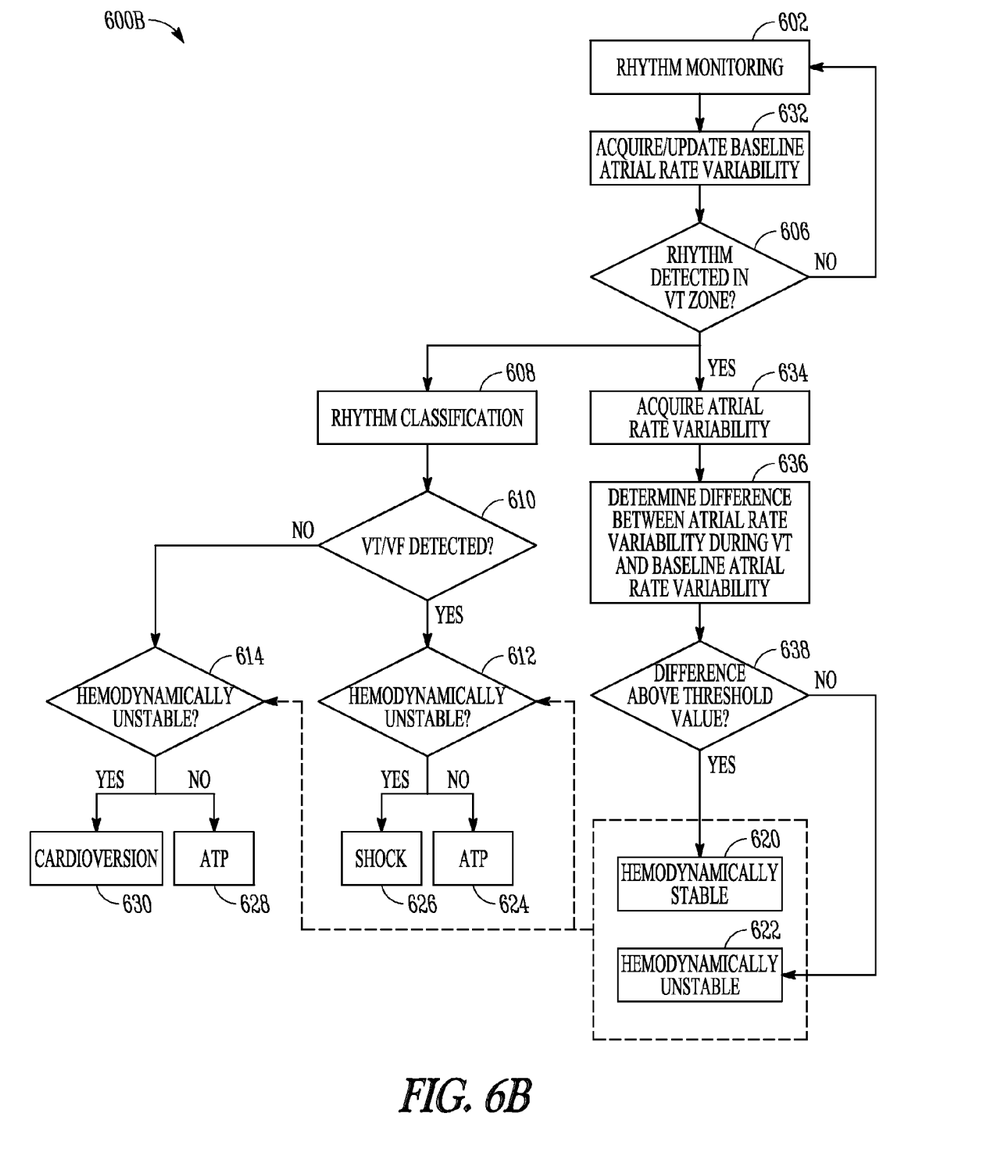
Figure 6C:
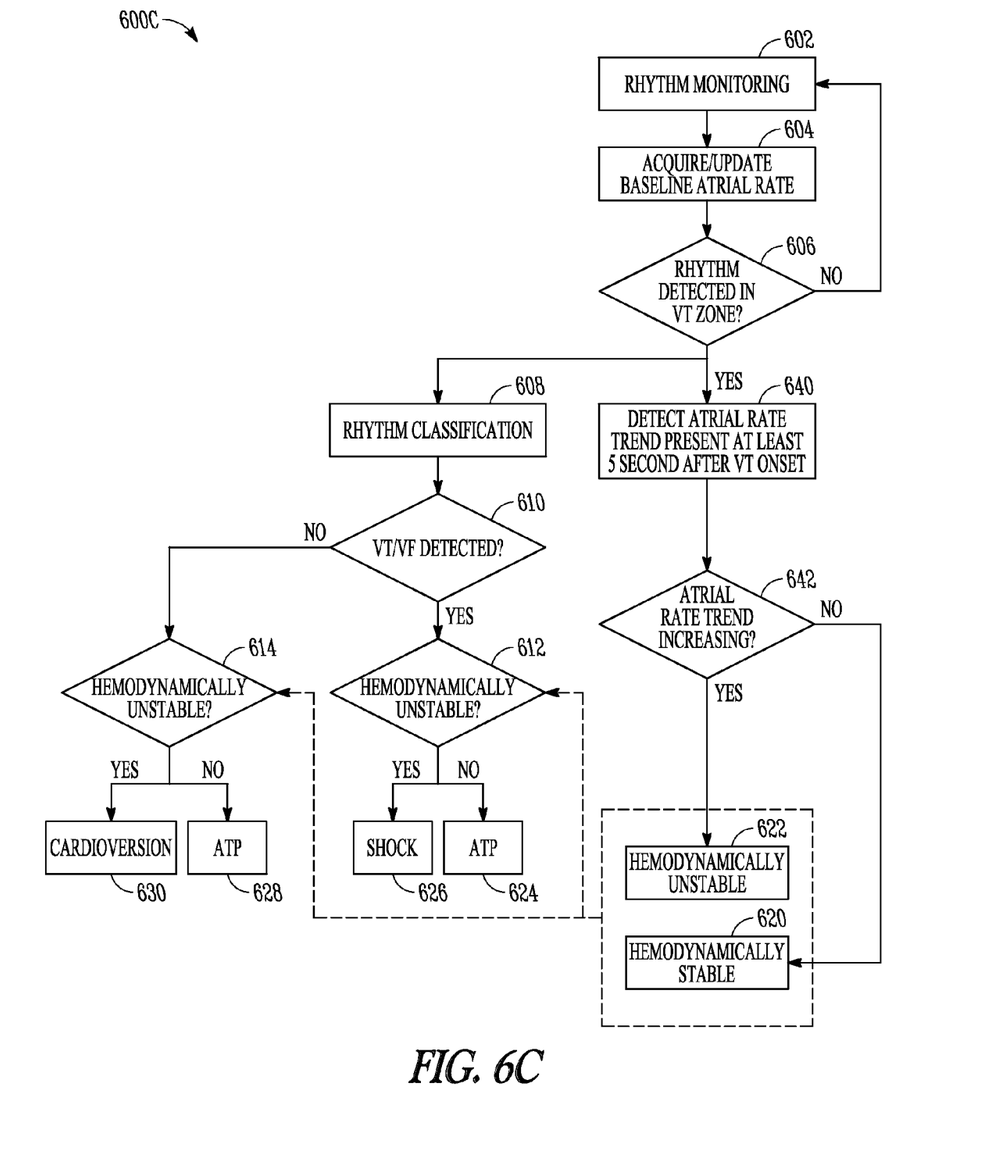

FIGS. 6A-6C show examples of methods for detecting hemodynamic stability during tachyarrhythmia using changes in atrial activation. FIG. 6A illustrates an example of a method 600A for differentiating between hemodynamically stable and unstable tachyarrhythmia using changes in atrial rate. At 602, cardiac rhythm is detected and monitored, such as by an implantable CRM device. At 604, baseline atrial rate measurements (e.g., atrial rate measurements taken just before tachyarrhythmia detection) are acquired or updated. In an example, atrial interval measurements can be taken instead of or in addition to atrial rate measurements. In an example, atrial rate or interval measurements can be taken over multiple cardiac cycles. At 606, if the detected cardiac rhythm is in the ventricular tachyarrhythmia zone, such as 120 to 200 beats per minute (bpm), then at 608, the detected tachyarrhythmia is classified. The tachyarrhythmia can be classified, for example, via analysis of the detected electrophysiological signal. At 610, if the tachyarrhythmia is classified as either ventricular tachyarrhythmia or ventricular fibrillation, then the process flows to 612. At 610, if the tachyarrhythmia is not classified as either ventricular tachyarrhythmia or ventricular fibrillation, then the process flows to 614.

At 606, if the detected cardiac rhythm is in the ventricular tachyarrhythmia zone, then at 616 an atrial rate measurement is acquired during the ventricular tachyarrhythmia. Atrial rate can be acquired at 616 concurrently with classification of the tachyarrhythmia at 608. At 618, it is determined whether the atrial rate during the ventricular tachyarrhythmia is substantially increased from the baseline atrial rate. In an example, at atrial rate during ventricular tachyarrhythmia that is more than 10% above the baseline atrial rate can be considered substantially increased. In an example, the atrial rate during ventricular tachyarrhythmia can be compared to a specified threshold value, or range of values, instead of or in addition to being compared to the baseline atrial rate. In an example, the specified threshold value can vary from patient to patient. If the atrial rate during tachyarrhythmia is not substantially increased from baseline (or is not above the threshold value), then at 620 the tachyarrhythmia is declared hemodynamically stable. If the atrial rate during tachyarrhythmia is substantially increased from baseline (or is above the threshold value), then at 622 the tachyarrhythmia is declared hemodynamically unstable. After the tachyarrhythmia has been declared hemodynamically stable at 620 or unstable at 622, the process flows back to 612 and 614. At 612, if the tachyarrhythmia has been declared hemodynamically stable, then at 624 anti-tachyarrhythmia pacing (ATP) is provided to the patient. At 612, if the tachyarrhythmia has been declared hemodynamically unstable, then at 626 shock therapy is provided to the patient. At 614, if the tachyarrhythmia has been declared hemodynamically stable, then at 628 ATP is provided to the patient. At 214, if the tachyarrhythmia has been declared hemodynamically unstable, then at 630 cardioversion is provided to the patient.

In an example, the patient's atrial rate measured during tachyarrhythmia and just prior to delivery of therapy can be compared to the atrial rate measured during or after the delivery of therapy. Such a comparison can be used to confirm or adjust the hemodynamic characterization of the tachyarrhythmia. For example, if ATP therapy is provided to a patient with declared hemodynamic stability, and the ATP therapy causes a decrease or stabilization of the atrial rate, then hemodynamic stability can be confirmed. If, on the other hand, the ATP therapy does not decrease or stabilize the atrial rate, then the patient's tachyarrhythmia may have been misclassified, and may actually be hemodynamically unstable. In this case, therapy can be changed, such as by stopping ATP and starting shock therapy or cardioversion.

FIG. 6B illustrates an example of a method 600B for differentiating between hemodynamically stable and unstable tachyarrhythmia using changes in atrial rate variability. At 602, cardiac rhythm is detected and monitored, such as by an implantable CRM device. At 632, baseline atrial rate variability measurements (e.g., atrial rate variability measurements taken just before tachyarrhythmia detection) are acquired or updated. In an example, atrial interval variability measurements can be taken instead of or in addition to atrial rate variability measurements. In an example, atrial rate/interval variability measurements can be taken over multiple cardiac cycles. At 606, if the detected cardiac rhythm is in the ventricular tachyarrhythmia zone, such as 120 to 200 beats per minute (bpm), then at 608, the detected tachyarrhythmia is classified. The tachyarrhythmia can be classified, for example, via analysis of the detected electrophysiological signal. At 610, if the tachyarrhythmia is classified as either ventricular tachyarrhythmia or ventricular fibrillation, then the process flows to 612. At 610, if the tachyarrhythmia is not classified as either ventricular tachyarrhythmia or ventricular fibrillation, then the process flows to 614.

At 606, if the detected cardiac rhythm is in the ventricular tachyarrhythmia zone, then at 634 an atrial rate variability measurement is acquired during the ventricular tachyarrhythmia. The atrial rate variability measurement can be acquired at 634 concurrently with classification of the tachyarrhythmia at 608. At 636, the difference between atrial rate variability during the tachyarrhythmia and the atrial rate variability at baseline is determined. At 638, the difference is compared to a threshold value. At 638, if the difference is not above the threshold value, then at 622 the tachyarrhythmia is declared hemodynamically unstable. At 638, if the difference is above the threshold value, then at 620 the tachyarrhythmia is declared hemodynamically stable. After the tachyarrhythmia has been declared hemodynamically stable at 620 or unstable at 622, the process flows back to 612 and 614. At 612, if the tachyarrhythmia has been declared hemodynamically stable, then at 624 anti-tachyarrhythmia pacing (ATP) is provided to the patient. At 612, if the tachyarrhythmia has been declared hemodynamically unstable, then at 626 shock therapy is provided to the patient. At 614, if the tachyarrhythmia has been declared hemodynamically stable, then at 628 ATP is provided to the patient. At 214, if the tachyarrhythmia has been declared hemodynamically unstable, then at 630 cardioversion is provided to the patient. As described above with respect to FIG. 6A, the patient's atrial rate variability before therapy can be compared to the atrial rate variability after therapy in order to confirm or adjust the hemodynamic stability characterization of the tachyarrhythmia and to adjust therapy as needed.

FIG. 6C illustrates an example of a method 600C for differentiating between hemodynamically stable and unstable tachyarrhythmia using changes in the atrial rate trend present at least 5 seconds after the onset of tachyarrhythmia. At 602, cardiac rhythm is detected and monitored, such as by an implantable CRM device. At 604, baseline atrial rate measurements (e.g., atrial rate measurements taken just before tachyarrhythmia detection) are acquired or updated. In an example, atrial interval measurements can be taken instead of or in addition to atrial rate measurements. In an example, atrial rate or interval measurements can be taken over multiple cardiac cycles. At 606, if the detected cardiac rhythm is in the ventricular tachyarrhythmia zone, such as 120 to 200 beats per minute (bpm), then at 608, the detected tachyarrhythmia is classified. The tachyarrhythmia can be classified, for example, via analysis of the detected electrophysiological signal. At 610, if the tachyarrhythmia is classified as either ventricular tachyarrhythmia or ventricular fibrillation, then the process flows to 612. At 610, if the tachyarrhythmia is not classified as either ventricular tachyarrhythmia or ventricular fibrillation, then the process flows to 614.

At 606, if the detected cardiac rhythm is in the ventricular tachyarrhythmia zone, then at 640 an atrial rate trend is detected at least 5 seconds after the onset of the ventricular tachyarrhythmia. The atrial rate trend can be detected at 640 concurrently with classification of the tachyarrhythmia at 608. At 642, it is determined whether the atrial rate trend at least 5 seconds after ventricular tachyarrhythmia onset is increasing or decreasing. If the atrial rate trend 5 seconds after tachyarrhythmia onset is decreasing, then at 620 the tachyarrhythmia is declared hemodynamically stable. If the atrial rate trend 5 seconds after tachyarrhythmia onset is increasing, then at 622 the tachyarrhythmia is declared hemodynamically unstable. After the tachyarrhythmia has been declared hemodynamically stable at 620 or unstable at 622, the process flows back to 612 and 614. At 612, if the tachyarrhythmia has been declared hemodynamically stable, then at 624 anti-tachyarrhythmia pacing (ATP) is provided to the patient. At 612, if the tachyarrhythmia has been declared hemodynamically unstable, then at 626 shock therapy is provided to the patient. At 614, if the tachyarrhythmia has been declared hemodynamically stable, then at 628 ATP is provided to the patient. At 214, if the tachyarrhythmia has been declared hemodynamically unstable, then at 630 cardioversion is provided to the patient. As described above with respect to FIG. 6A, the patient's atrial rate variability before therapy can be compared to the atrial rate variability after therapy in order to confirm or adjust the hemodynamic stability characterization of the tachyarrhythmia and to adjust therapy as needed.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. A method comprising
sensing an atrial activation of a subject;
detecting that a tachyarrhythmia is present in the subject;
comparing a characteristic of the atrial activation present just before the tachyarrhythmia was detected to a characteristic of the atrial activation during the detected tachyarrhythmia, wherein comparing includes:
determining a difference between an atrial rate variability present just before the tachyarrhythmia was detected to an atrial rate variability during the detected tachyarrhythmia; and
comparing the difference to a threshold value; and
using the comparison to determine a hemodynamic stability characteristic of the tachyarrhythmia, wherein determining the hemodynamic stability characteristic includes:
when the difference is above the threshold value, declaring that the tachyarrhythmia is hemodynamically stable; and
when the difference is below the threshold value, declaring that the tachyarrhythmia is hemodynamically unstable.

2. The method of claim 1, wherein the characteristic of the atrial activation includes at least one of: an atrial rate or interval, or an atrial rate or interval variability.

3. The method of claim 1, comprising:
comparing an atrial rate present just before the tachyarrhythmia was detected to an atrial rate during the detected tachyarrhythmia;
determining whether the atrial rate during the detected tachyarrhythmia is substantially increased from the atrial rate present just before the tachyarrhythmia was detected;
declaring that the tachyarrhythmia is hemodynamically unstable upon determining that the atrial rate during the detected tachyarrhythmia is substantially increased from the atrial rate present just before the tachyarrhythmia was detected; and
declaring that the tachyarrhythmia is hemodynamically stable upon determining that the atrial rate during the detected tachyarrhythmia is not substantially increased from the atrial rate present just before the tachyarrhythmia was detected.

4. The method of claim 1, comprising using the hemodynamic stability characteristic of the tachyarrhythmia to control therapy provided to the subject.

5. The method of claim 4, comprising providing anti-tachyarrhythmia pacing to the subject when the tachyarrhythmia is hemodynamically stable.

6. The method of claim 4, comprising:
providing shock therapy to the subject when the tachyarrhythmia is hemodynamically unstable; and
withholding shock therapy when the tachyarrhythmia is hemodynamically stable.

7. The method of claim 4, comprising:
comparing an atrial characteristic present during the tachyarrhythmia and just before delivery of therapy to an atrial characteristic present during or after delivery of therapy; and
using the comparison to do at least one of:
confirming or detecting a change in the hemodynamic stability characteristic of the tachyarrhythmia, or
adjusting the therapy to the subject.

8. The method of claim 1, comprising:
detecting an atrial rate trend present at least 5 seconds after the start of the detected tachyarrhythmia;
determining whether the atrial rate trend present at least 5 seconds after the start of the detected tachyarrhythmia is increasing or decreasing; and
using the determination to declare a hemodynamic stability characteristic of the tachyarrhythmia.

9. The method of claim 8, comprising:
declaring that the tachyarrhythmia is hemodynamically unstable when it is determined that the atrial rate trend present at least 5 seconds after the start of the detected tachyarrhythmia is increasing; and declaring that the tachyarrhythmia is hemodynamically stable when it is determined that the atrial rate trend present at least 5 seconds after the start of the detected tachyarrhythmia is decreasing.

10. The method of claim 8, comprising:
providing therapy to the subject;
using the hemodynamic stability characteristic of the tachyarrhythmia to control therapy provided to the subject;
providing anti-tachyarrhythmia pacing to the subject when the tachyarrhythmia is hemodynamically stable;
providing shock therapy to the subject when the tachyarrhythmia is hemodynamically unstable; and
withholding shock therapy when the tachyarrhythmia is hemodynamically stable.

11. A method comprising
sensing an atrial rate of a subject;
detecting that a tachyarrhythmia is present in the subject;
detecting an atrial rate trend present at least 5 seconds after the start of the detected tachyarrhythmia;
determining whether the atrial rate trend present at least 5 seconds after the start of the detected tachyarrhythmia is increasing or decreasing; and
using the determination to declare a hemodynamic stability characteristic of the tachyarrhythmia, wherein declaring the hemodynamic stability characteristic includes:
    declaring that the tachyarrhythmia is hemodynamically unstable upon determining that the atrial rate trend present at least 5 seconds after the start of the detected tachyarrhythmia is increasing; and
    declaring that the tachyarrhythmia is hemodynamically stable upon determining that the atrial rate trend present at least 5 seconds after the start of the detected tachyarrhythmia is decreasing.

12. The method of claim 11, comprising:
using the hemodynamic stability characteristic of the tachyarrhythmia to control therapy provided to the subject;
providing anti-tachyarrhythmia pacing to the subject when the tachyarrhythmia is hemodynamically stable;
providing shock therapy to the subject when the tachyarrhythmia is hemodynamically unstable; and
withholding shock therapy when the tachyarrhythmia is hemodynamically stable.

13. A method comprising
sensing an atrial activation of a subject;
detecting that a tachyarrhythmia is present in the subject;
comparing a characteristic of the atrial activation present just before the tachyarrhythmia was detected to a characteristic of the atrial activation during the detected tachyarrhythmia, wherein the characteristic of the atrial activation includes an atrial rate;
determining whether the atrial rate during the detected tachyarrhythmia is increased from the atrial rate present just before the tachyarrhythmia was detected; and
using the comparison to determine a hemodynamic stability characteristic of the tachyarrhythmia, including:
    declaring that the tachyarrhythmia is hemodynamically unstable upon determining that the atrial rate during the detected tachyarrhythmia is substantially increased from the atrial rate present just before the tachyarrhythmia was detected; and
    declaring that the tachyarrhythmia is hemodynamically stable upon determining that the atrial rate during the detected tachyarrhythmia is not substantially increased from the atrial rate present just before the tachyarrhythmia was detected.

14. The method of claim 13, wherein the characteristic of the atrial activation includes an atrial rate or interval variability.

15. The method of claim 13, comprising:
determining a difference between an atrial rate variability present just before the tachyarrhythmia was detected to an atrial rate variability during the detected tachyarrhythmia;
comparing the difference to a threshold value;
when the difference is above the threshold value, declaring that the tachyarrhythmia is hemodynamically stable; and
when the difference is below the threshold value, declaring that the tachyarrhythmia is hemodynamically unstable.

16. The method of claim 13, comprising using the hemodynamic stability characteristic of the tachyarrhythmia to control therapy provided to the subject.

17. The method of claim 16, comprising providing anti-tachyarrhythmia pacing to the subject when the tachyarrhythmia is hemodynamically stable.

18. The method of claim 16, comprising:
providing shock therapy to the subject when the tachyarrhythmia is hemodynamically unstable; and
withholding shock therapy when the tachyarrhythmia is hemodynamically stable.

* * * * *